(12) United States Patent
Bhawalkar et al.

(10) Patent No.: US 12,336,869 B2
(45) Date of Patent: Jun. 24, 2025

(54) SUPPORT SYSTEM FOR TREATMENT DEVICE

(71) Applicant: Avava, Inc., Waltham, MA (US)

(72) Inventors: Jayant Bhawalkar, Auburndale, MA (US); Ryan Martin, Carlisle, MA (US); Patrick Shaughnessy, Boston, MA (US); Lewis Levine, Marlborough, MA (US); Andrew Ziegler, Arlington, MA (US); Michael Stephen Rafferty, Madison, WI (US); Andrew Jones, Cambridge, MA (US); Ryan Bayne, Cambridge, MA (US); Zachary Michael Zlevor, La Grange Park, IL (US)

(73) Assignee: Avava, Inc., Waltham, MA (US)

( * ) Notice: Subject to any disclaimer, the term of this patent is extended or adjusted under 35 U.S.C. 154(b) by 0 days.

(21) Appl. No.: 18/827,792

(22) Filed: Sep. 8, 2024

(65) Prior Publication Data

US 2024/0423754 A1 Dec. 26, 2024

Related U.S. Application Data

(63) Continuation of application No. PCT/US2024/022822, filed on Apr. 3, 2024.

(60) Provisional application No. 63/458,560, filed on Apr. 11, 2023.

(51) Int. Cl.
*A61B 90/50* (2016.01)
*A61B 18/20* (2006.01)
*A61B 18/00* (2006.01)

(52) U.S. Cl.
CPC .............. *A61B 90/50* (2016.02); *A61B 18/20* (2013.01); *A61B 2018/0091* (2013.01)

(58) Field of Classification Search
CPC .. A61B 90/50; A61B 18/20; A61B 2018/0091
USPC ............................................................ 606/4
See application file for complete search history.

(56) References Cited

U.S. PATENT DOCUMENTS

| 4,144,888 A | 3/1979 | Malyshev et al. |
| 5,300,067 A | 4/1994 | Nakajima et al. |
| 5,346,489 A * | 9/1994 | Levy .................... A61C 1/0046 606/15 |

(Continued)

FOREIGN PATENT DOCUMENTS

| JP | 2006254986 A | 9/2006 |
| WO | 2024215539 A1 | 10/2024 |

*Primary Examiner* — Aaron F Roane
(74) *Attorney, Agent, or Firm* — Mintz Levin Cohn Ferris Glovsky and Popeo, P.C.

(57) ABSTRACT

Support systems for handpieces are provided. The support system includes a boom assembly having a rigid anchor base and a flexible rod having proximal and distal ends, and a connection assembly having a proximal end configured to couple to the distal end of the flexible rod and a distal end configured to couple to the handpiece. The flexible rod is pivotally secured at the proximal end thereof to the anchor base, and the flexible rod has a flexibility that increases from a distal end to the proximal end thereof. The connection assembly is configured to enable the handpiece to rotate in at least two degrees of freedom. The boom assembly is configured to support the connection assembly and the handpiece such that the connection assembly and the handpiece rest in a neutral position.

18 Claims, 10 Drawing Sheets

(56) References Cited

U.S. PATENT DOCUMENTS

| | | | |
|---|---|---|---|
| 2008/0091066 A1* | 4/2008 | Sholev | A61B 90/50 600/112 |
| 2013/0221184 A1 | 8/2013 | Odaka et al. | |
| 2020/0253678 A1* | 8/2020 | Hulford | A61B 34/37 |
| 2021/0022769 A1* | 1/2021 | Mark | A61B 34/20 |
| 2021/0138261 A1 | 5/2021 | Bhawalkar et al. | |
| 2021/0213298 A1 | 7/2021 | Takata et al. | |
| 2021/0228237 A1* | 7/2021 | De Juan | A61B 17/3201 |

* cited by examiner

SUPPORT SYSTEM FOR TREATMENT DEVICE

CROSS-REFERENCE TO RELATED APPLICATIONS

This application is a by-pass continuation application, which claims the benefit of Application No. PCT/US24/22822, filed on Apr. 3, 2024, entitled "SUPPORT SYSTEM FOR TREATMENT DEVICE" which claims the benefit of U.S. Provisional Application No. 63/458,560, filed Apr. 11, 2023, and entitled "SUPPORT SYSTEM FOR TREATMENT DEVICE." The entire contents of which are hereby incorporated herein by reference in its entirety.

BACKGROUND

Laser-based treatment devices can be effective in treating numerous ailments. During treatment procedures, a treatment operator, such as a physician or an aesthetician, moves such treatment devices over the affected tissue while the treatment device irradiates the affected tissue with a precise dose of energy. Too much energy delivered to the affected tissue can result in potential harm to the patient, while too little energy delivered to the affected tissue can result in an ineffective treatment. In order to maximize an efficacy of the treatment, the treatment operator must carefully control the treatment device, which can weigh several pounds or more, to deliver the correct dose of radiation over the course the treatment procedure, which can last for thirty minutes or longer. Over the course of a treatment procedure, a treatment operator can become fatigued, which may detrimentally affect the patient. Further, a treatment operator may have multiple successive procedures in a single day, which can further exacerbate issues associated with operator fatigue, resulting in inadequate or even harmful irradiation of a patient with the treatment devices.

To combat the issue of fatigue, certain support systems and armatures have been developed to take the load from the operator. However, these systems typically utilize an articulated arm with one or more manually adjustable joints from which the treatment device freely hangs. Such systems still require the treatment operator to fully support the weight of the treatment device and the associated cables the in order to control finer movements of the treatment device during a treatment procedure. Accordingly, there remains a need for improved support systems to assist a treatment operator during treatment procedures.

SUMMARY

Support systems for handpieces are provided.

In an embodiment, a support system for a handpiece is provided, including a boom assembly having a rigid anchor base and a flexible rod having proximal and distal ends, and a connection assembly having a proximal end configured to couple to the distal end of the flexible rod and a distal end configured to couple to the handpiece. The flexible rod can be pivotally secured at the proximal end thereof to the anchor base. The flexible rod can have a flexibility that increases from the proximal end to the a distal end thereof the connection assembly being configured to enable the handpiece to rotate in at least two degrees of freedom. The boom assembly can be configured to support the connection assembly and the handpiece such that the connection assembly and the handpiece rest in a neutral position.

The support system can vary in a number of ways. For example, the support system can include a handpiece coupled to the connection assembly. In some aspects, the handpiece can be a laser treatment device for medical and/or cosmetic procedures. For example, the connection assembly and handpiece can be maneuverable with a minimal effort in an envelope surrounding the neutral position. For example, the connection assembly can be configured to enable the handpiece to rotate in three degrees of freedom. Each of the degrees of freedom can be substantially orthogonal to the other degrees of freedom. For example, the flexible rod can have a consistent taper from the proximal end thereof to the distal end thereof, and a flexibility of the rod can increase proportionally with the constant taper from the proximal end to the distal end. The flexible rod can also be hollow. For example, an actuatable lift coupled to the anchor base, which can be configured to extend in an upward direction and retract in a downward direction. Moreover, the actuatable lift can be extendable by between about 18 and 30 inches. Further, the actuatable lift can include a fulcrum extension configured to support the rigid anchor base at an angle relative thereto. In some aspects, the rigid anchor base can be configured to slide relative to the fulcrum extension when the actuatable lift is extended and retracted such that the angle is configured to move between about 120 degrees and 180 degrees.

In another embodiment, a support system for a handpiece is provided, including a cart including an extendable lift movable between an extended position and a retracted position, a boom assembly coupled to the extendable lift, and a connection assembly coupled to a distal end of the flexible rod. The boom assembly can include a rigid anchor base, and a flexible rod coupled to a proximal end of the rigid anchor portion at a proximal end thereof. The connection assembly can be configured to couple to the handpiece such that the handpiece can rotate in at least two degrees of freedom relative thereto.

The support system can vary in a number of ways. For example, the boom assembly and the connection assembly can be configured to support the handpiece at a neutral position, and the handpiece can be maneuverable with a minimal effort in an envelope surrounding the neutral position. In some variations, the force required to move the handpiece when the handpiece is within the envelope can be less than or equal to about 0.5 lbF. For example, the connection assembly can be configured to enable the handpiece to rotate in three degrees of freedom, and each of the degrees of freedom can be substantially orthogonal to the other degrees of freedom. For example, the support system can include a plurality of transport lines running along the boom assembly. Respective first ends of the plurality of transport lines can be disposed in the cart, and respective second ends can be configured to connect to the handpiece. Moreover, the plurality of transport lines can include at least one fluid line. In some variations, the at least one fluid line can include a first fluid line configured to transport a first fluid and a second fluid line configured to transport a second fluid different than the first fluid. In some aspects, the first fluid is a de-humidified gas and the second fluid is a coolant.

BRIEF DESCRIPTION OF THE DRAWINGS

Embodiments of the disclosure will be more fully understood from the following detailed description taken in conjunction with the accompanying drawings, in which.

Figure 1:
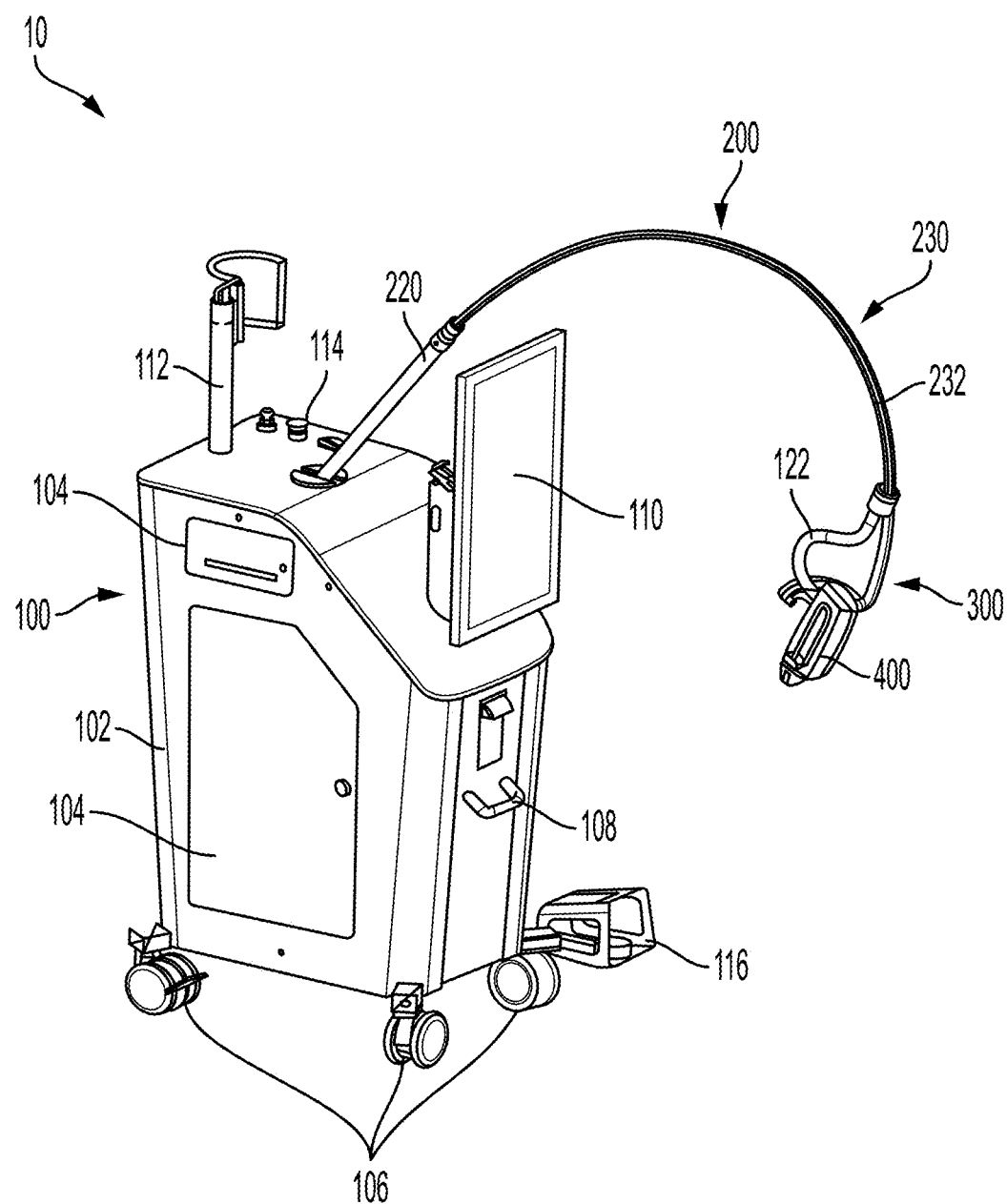
FIG. 1 depicts a perspective view of a support system, according to an embodiment.

It is noted that the drawings are not necessarily to scale. The drawings are intended to depict only typical aspects of the subject matter disclosed herein, and therefore should not be considered as limiting the scope of the disclosure. The systems, devices, and methods specifically described herein and illustrated in the accompanying drawings are non-limiting exemplary embodiments.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present disclosure is defined solely by the claims. The features illustrated or described in connection with one exemplary embodiment may be combined with the features of other embodiments. Such modifications and variations are intended to be included within the scope of the present disclosure.

Methods of treating various conditions, such as for medical and/or cosmetic purposes, can be carried out using the systems described herein. It is understood that, although such methods can be conducted by a physician, non-physicians, such as aestheticians and other suitably trained personnel may use the systems described herein to treat various conditions with and without the supervision of a physician.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Various ailments and maladies can be treated using precise doses of electromagnetic radiation (EMR) deposited on afflicted tissue by a laser treatment device. In these treatment procedures, a treatment operator, such as a physician or aesthetician must move a weighty treatment device (also referred to as a handpiece) over the affected tissue in order to properly dose the tissue over the course of a procedure, which could last for thirty minutes or more. The weight of the handpiece and the fine movements required over prolonged duration of the treatment procedure (or in multiple, successive procedures with more than once patient) can cause operator fatigue, which can result in loss in efficacy of the treatment procedure. Support systems for laser-based treatment devices, and methods associated therewith, that address these needs are described herein. The support systems can support the handpiece in a region near a patient and in such a way as to provide for fine motor control of the handpiece by the operator while the support systems take the load of the handpiece off the operator. Laser treatment devices and handpieces that are compatible with the support systems can vary, and exemplary devices and handpieces are disclosed in U.S. Patent Application Publication No. 2021/0138261, entitled "Feedback Detection for a Treatment Device," which is hereby incorporated by reference herein in its entirety.

Such devices can be applicable to a wide variety of medical and/or cosmetic procedures. Reference to a specific kind of procedure is exemplary only, and should not be construed to limit the overall disclosure. Various medical and/or cosmetic procedures involve prolonged and precise handling by a treatment operator, and fatigue can be detrimental in such procedures regardless of the type of tissue or ailment being treated, the specific operator, etc. The devices and methods described herein can therefore be widely applicable to provide increased stamina and control to operators generally.

In general, the support systems described herein include a boom assembly coupled to an anchor base. The boom assembly can take on a variety of forms and in general, the boom assembly can comprise an articulable and steady portion coupled to a flexible portion, and the flexible portion can support an orientation assembly, like a gimbal system, to ultimately support the handpiece during a treatment procedure, while also allowing for rotation of the handpiece about one, two, or three degrees of freedom so as not to limit maneuverability thereof during a procedure, and ultimately so as not to limit the quality of a procedure.

The anchor base can provide a support for the boom assembly as the handpiece is supported by the boom assembly and maneuvered during a treatment procedure. Operation of the handpiece requires various connections, cables, and lines, and the anchor base can also provide a place to stow components of the system that are required to operate the device during the treatment procedure, such as a power source, a chiller assembly (e.g., cooling lines) for handpieces that cool tissue to be treated, an EMR source, and more. The anchor base can also include an actuator that can raise or lower the boom assembly, which can grant a treatment operator more flexibility during a treatment procedure.

When the support systems are not in use, they can be placed in a docked position in which the handpiece is set within a dock located on the boom assembly to minimize the overall footprint of the support systems. When needed, the handpiece can be undocked and manipulated by an operator as needed for a given procedure.

Referring now to FIG. 1, a support system 10 for use with laser treatment devices and handpieces according to some embodiments is shown. The support system 10, shown in an undocked position, can generally include an anchor base 100, a boom assembly 200 coupled thereto, and a connection assembly 300 that is configured to support a handpiece, such as a handpiece 400. Together, the anchor base 100, boom assembly 200, and connection assembly 300 can support the handpiece 400 during a procedure to minimize and/or eliminate the fatigue of a treatment operator, as described above. As shown, the support system 10 is placed within an undocked position in which the handpiece 400 is uncoupled from anything other than the connection assembly 300 to which it is always mounted. This undocked position, as introduced above, exists in contrast to a docked position of the support system 10 in which the handpiece is secured within a dock (not pictured). The docked position will be described in greater detail below, and the dock (not pictured) will be described with reference to the docked position.

The anchor base 100 can take on a variety of forms, including the form of a cabinet having a substantially hollow anchor frame 102 with one or more doors 104 located thereon that provide access to an interior of the anchor base 100. The anchor base 100 can be supported by various mechanisms, including selectively lockable wheels 106 (e.g., castors), which can enable the anchor base to remain fixed or moved as required. The anchor base 100 can also include one or more handles 108 to facilitate movement thereof, and the one or more handles 108 can be located on the anchor base 100 in positions that allow for the treatment operator to adjust the position of the anchor base 100 while remaining seated, such as during a procedure.

The anchor base 100 can also include a display 110 that can relay various information related to the treatment procedure and other information. The display 110 can be mounted or otherwise coupled to the anchor base 100 so that it can be adjusted for convenience as needed. A handpiece dock 112 can be located on the anchor base 100, which can be used to stow the handpiece 400 when it is not in use. As seen in FIG. 1, for example, when the handpiece 400 is in a ready position, it rests some distance away from the anchor base 100, which may not always be desirable. Instead of resting in an outward position, the handpiece 400 can be placed within the dock 112 to reduce the overall footprint of the support system 10. The anchor base 100 can also include various inputs 114 located thereon, such as a key-start, lockout mechanism, controls, etc. One such input can be a foot pedal 116, which can be operated by the treatment operator to turn the handpiece on or off as needed during a treatment procedure.

As briefly explained above, the anchor base 100 can house one or more systems necessary for the treatment procedure, including an EMR source (not shown), a chiller 118, a power source 120, an air-drying system (not shown), and various electronics for controlling the handpiece 400. Also include within the anchor base 100 is a lift system 210, which is part of the boom assembly 200 and will be described below. These systems can be seen in the cross-section of the anchor base 100 depicted in FIG. 2. The one or more systems can be housed in an interior of the anchor base 100 that is accessible through the one or more doors 104, and various connectors 122, such as cables and tubing, can run along the boom assembly 200 and can connect with the handpiece 400. As mentioned above, the handpiece can include an optical window that includes a coolant running therethrough. Coolant can run through the connectors 122 to be chilled by the chilling assembly in order to cool the tissue being treated in the treatment procedure. The connectors 122 can include cables to transmit power to the handpiece 400 from the power source 120, and tubing that transports the chilled coolant to the optical window. In some variations, the connectors 122 can also include tubing that transports dehumidified air. During the treatment operation, condensation can appear on the chilled optical window, which can disrupt the transmission of a treatment beam therethrough. Introducing dehumidified gas and/or air to the chilled optical window via the connectors 122 can prevent condensation from building up. The connectors 122 can run along the boom assembly 200 to electrically and fluidly join the handpiece 400 to the systems located in the anchor base 100 as will be described in greater detail below. In some aspects, the connectors 122 can be designed to facilitate a quick-release of the handpiece 400, such as when servicing the handpiece 400 becomes necessary or if a variety of handpieces 400 are used with the support system 100.

Figure 3:
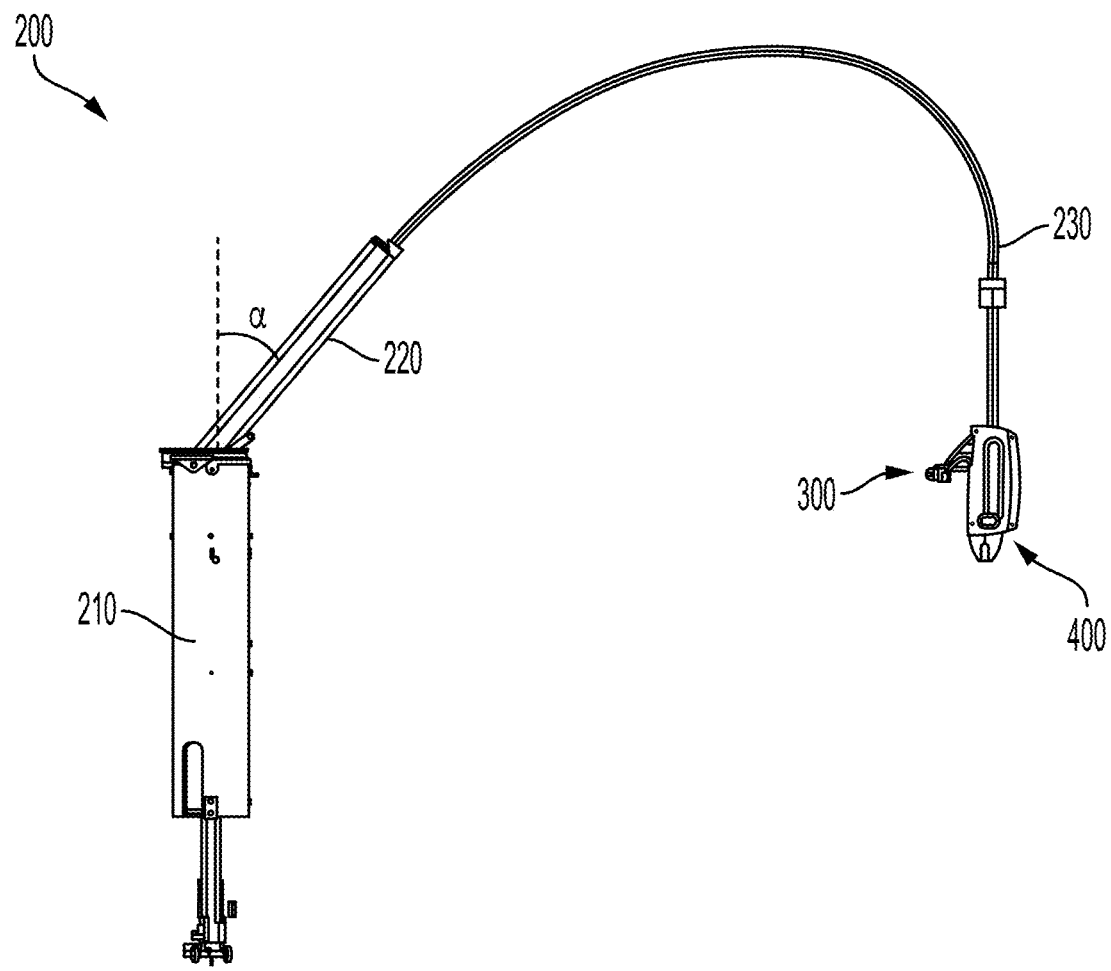
FIG. 3 depicts a side view of a boom assembly usable with the support system of FIG. 1.

The support system 10 can also include a boom assembly 200, which can be coupled to the anchor base 100 and can support the handpiece 400 during a treatment operation. The boom assembly can be generally articulable by a treatment operator while simultaneously supporting at least a majority of the weight of the handpiece 400. The boom assembly 200 can be seen in FIG. 3 isolated from the anchor base 100, while also being still coupled to both the connection assembly 300 and the handpiece 400. Generally, the boom assembly 200 can include a lift system 210, a rigid support base 220, and a flexible rod 230.

Figure 2:
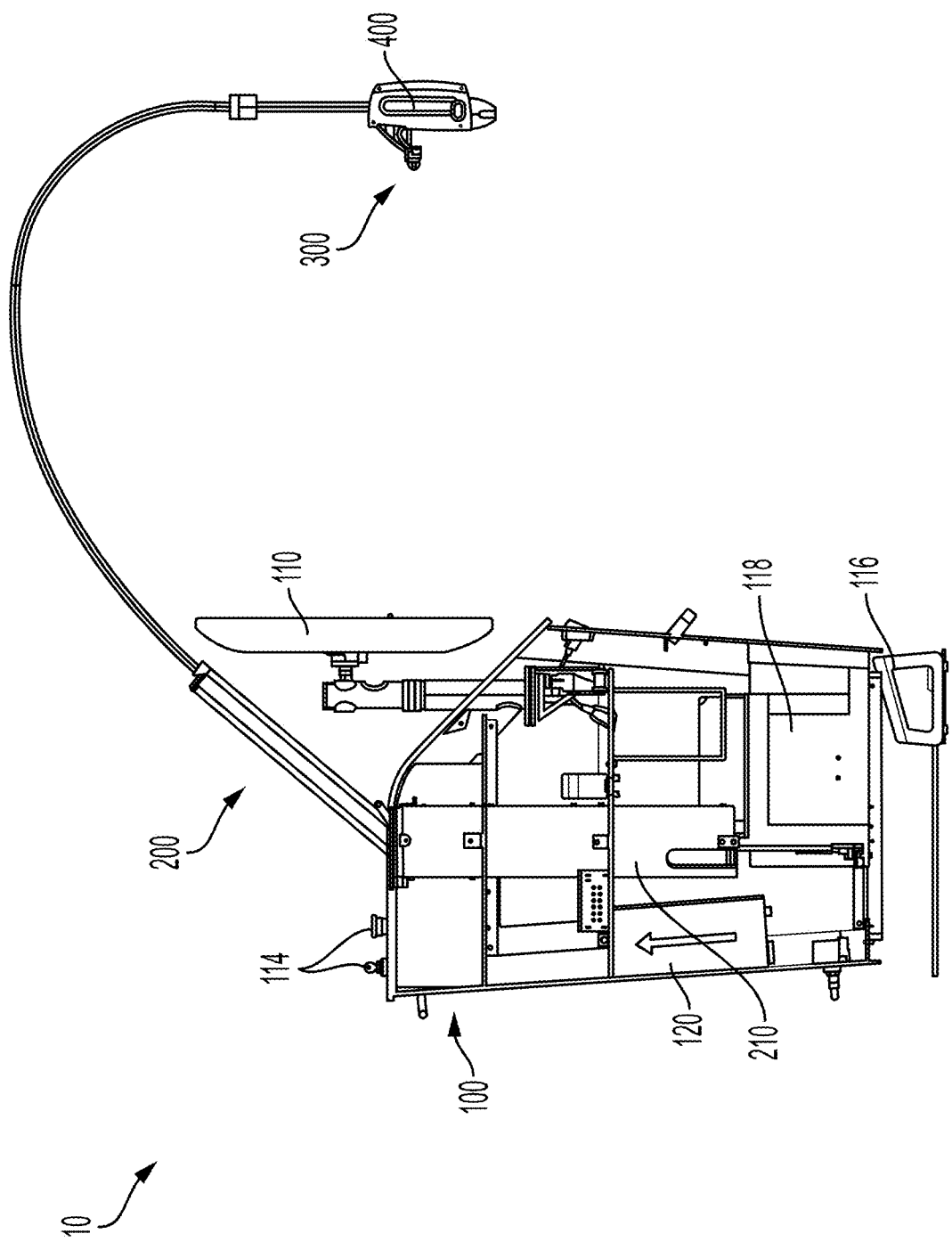
FIG. 2 depicts a cross-sectional view of the support system of FIG. 1.
Figure 4:
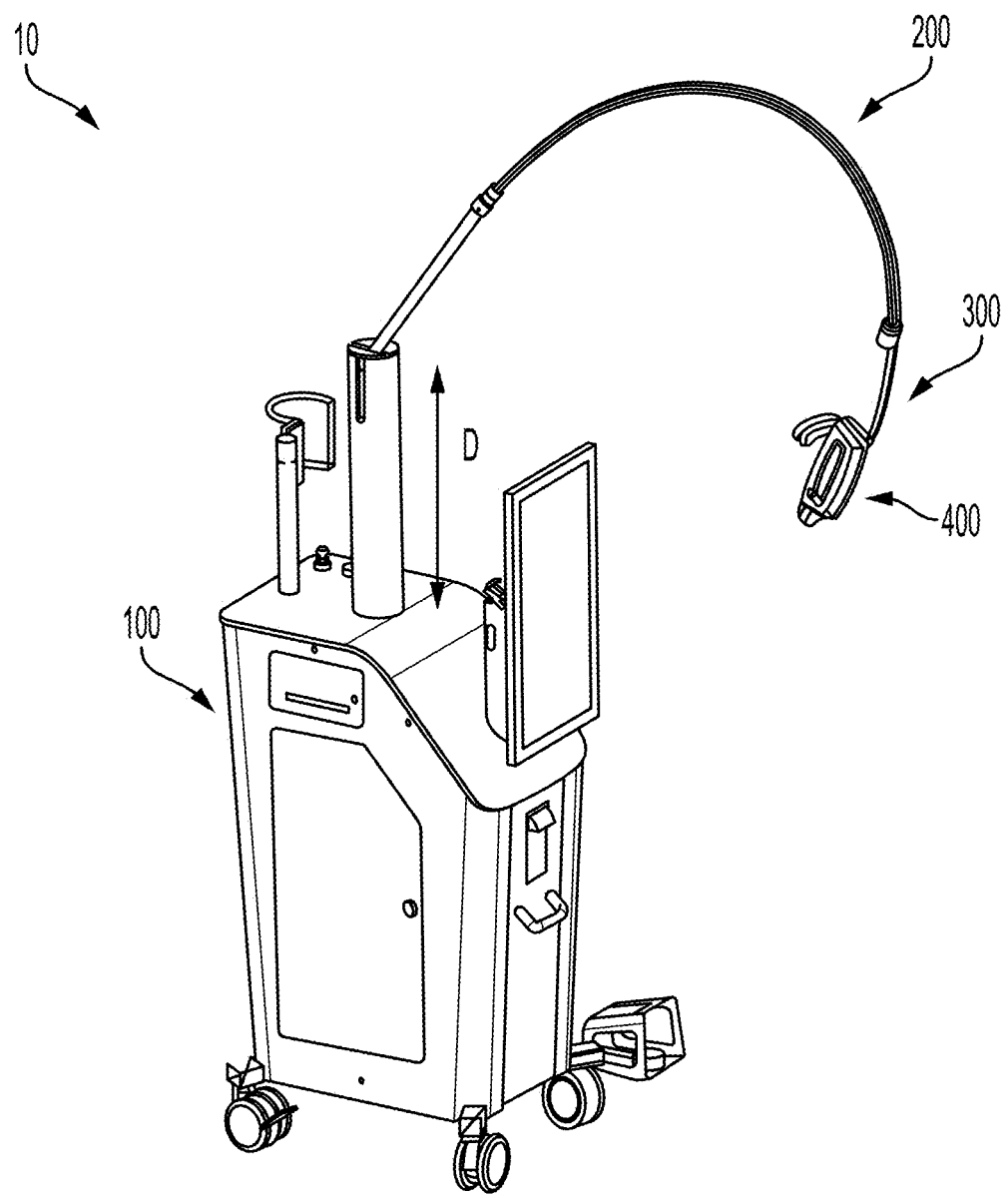
FIG. 4 is a perspective view of the support system of FIG. 1, having a lift system in an extended position.

The lift system 210 can be mostly located within the anchor base 100 and can extend and retract as needed in order to raise and lower the handpiece 400 to a more preferable position for the treatment procedure. The lift system 210 can be a mechanical system like a rail system and the like. In other variations, the lift system 210 can be pneumatic or hydraulic as well. When the lift system 210 is fully retracted, a top of the lift system 210 can be essentially flush with a top of the anchor base, as seen in FIGS. 1 and 2, for example. When extension of the lift system 210 is desired, the treatment operator or another person, can extend the lift system 210 via the one or more inputs 114, over a distance D (shown in FIG. 4) up to an upper limit. Over this range, the lift system 210 can provide up to an additional 18-30 inches of height or more, and in some variations, about 20 inches of height or more.

The rigid support base 220 can be coupled to the lift system 210 in a pivotal and/or sliding manner so that the rigid support base 220 can be moved relative to the lift system 210 and the anchor base 100 as desired. For example, a proximal end of the rigid support base 220 can be coupled to an internal lift mechanism (not shown) in the lift system 210 so that the rigid support base 220 can be extended or retracted to pivot with the lift system 210 and/or relative to the lift system 210, and provide a range of angles over which the lift system can be pivoted. For example, the rigid support base 220 can be maneuvered over a range at angle α (seen in FIGS. 3 and 8-10) between about 5 degrees and 50 degrees relative to vertical. In some variations, the angle α can be between 0 degrees relative to vertical and 90 degrees relative to vertical, and the rigid support base 220 can be deliberately placed to any value within the entire range of possibilities.

Figure 5:
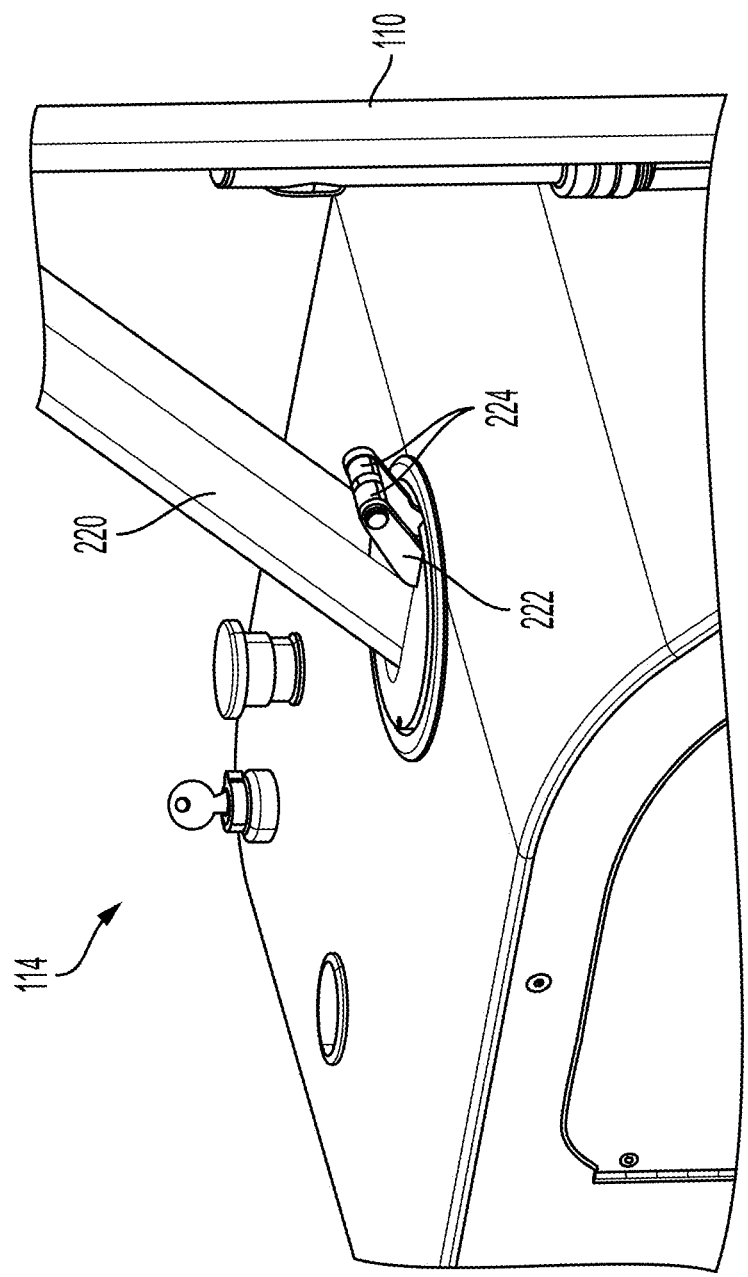
FIG. 5 is a partial perspective view of a top portion of the support system of FIG. 1.

To assist in extending, retracting, and pivoting the rigid support base 220, a spring-loaded guide 222, seen, for example, in FIG. 5, can be located at the top of the lift system 210. The spring-loaded guide 222 can be spring-biased or otherwise mechanically biased toward the rigid support base 220. As the rigid support base 220 is extended and retracted relative to the lift system 210, the spring-loaded guide 222 can flex and pivot to compensate for an increased load placed upon itself, acting as a fulcrum for the rigid support base 220. Moreover, to ease movement of the rigid support base 220 relative thereto, the spring-loaded guide 222 can feature one or more rollers 224 that can roll freely to minimize frictional contact between the spring-loaded guide 222 and the rigid support base 220.

The boom assembly 200 can also include the flexible rod 230, which can be a flexible element affixed to the rigid support base 220. A proximal end of the flexible rod 230 can be coupled closer to the proximal end of the rigid support base 220 so that when the flexible rod 230 is flexed under the weight of the handpiece 400, the rigid support base 220 can take some of that load to stabilize the handpiece 400 and the boom assembly 200 itself. Essentially, the flexible rod 230 can operate similarly to a fishing rod under load. When the handpiece 400 is attached to the flexible rod 230 and in the undocked position, the flexible rod 230 will flex to a certain degree under the weight of the handpiece 400 and the angle α at which the rigid support base 220 is placed, depending upon the properties of the flexible rod 230. Eventually, the handpiece 400 will come to an equilibrium or neutral position in which it is at rest. Modifying the properties of the flexible rod 230 so that it is made of a different material, has a different geometry and flexion properties, etc. can alter the location of this neutral position, and manipulating the angle α and/or the distance D can also affect the exact location of this neutral position relative to the rest of the support system 10. For example, if the flexible rod 230 becomes more rigid and the handpiece remains the same, the handpiece 400 would not flex the rod to the same degree. This may result in a neutral position that is relative higher and/or further from the anchor base 100.

In general, the handpiece 400 can weigh about 2 lbs., give or take about 0.25 lbs. The flexible rod 230 can be designed and dimensioned based upon the overall weight of the handpiece 400 in order to ensure that the neutral position is in a practical location relative to the rest of the system for an operator to effectively make use of the support system 10. Specifically, in some embodiments, the flexible rod 230 can be substantially hollow and can have a consistent taper from a proximal end thereof to a distal end thereof. A flexibility of the rod can increase proportionally with the constant taper of the flexible rod 230, such that the distal end is substantially more pliable and flexible than the proximal end. The flexible rod 230, in some variations, can even be a fishing rod without the eyelets and other components used for fishing. The similarities between flexible rod 230 and fishing rods can be similar enough that the flexible rod 230 can be described in terms of fishing rods, including. For example, the flexible rod 230 can have a length of about seven feet, give or take about one foot, and a diameter at a distal end (also called a butt diameter) of between about 0.5 and 0.55 inches, or in some cases, about 0.527 inches. A property known as "action" can describe the way a fishing rod flexes under a given load, and this action can be described in terms including slow, medium, and fast, with slow action equating to a larger degree of flexion under a given load and slow action equating to a smaller degree of flexion under the same given load. The flexible rod 230 can be said to have a medium-fast action. The flexible rod 230 can be made from a number of materials. To obtain consistent performance with a given handpiece 400, the exact dimensions of the flexible rod 230 may vary slightly as a result of different properties of materials. The materials can include fiberglass, bamboo, poplar, carbon fiber, bent sheet metal, graphite, or other materials, including various woods, metals, plastics, composites, etc. that yield similar performance.

As mentioned above, the connectors 122 can transmit energy and one or more fluids to the handpiece 400 that are necessary for the treatment procedure and proper operation thereof. The connectors 122 can take on a variety of forms, such as cables and/or tubing, which can run along the boom assembly 200 through the lift system 210, through the rigid support base 220, and along the flexible rod 230. The connectors 122 can be coupled to the flexible rod 230 in a number of ways. For example, the flexible rod and the connectors 122 can be contained within a sheath 232, which can extend the entire length of the flexible rod 230 between the rigid support base 220 and the connection assembly 300.

Figure 6:
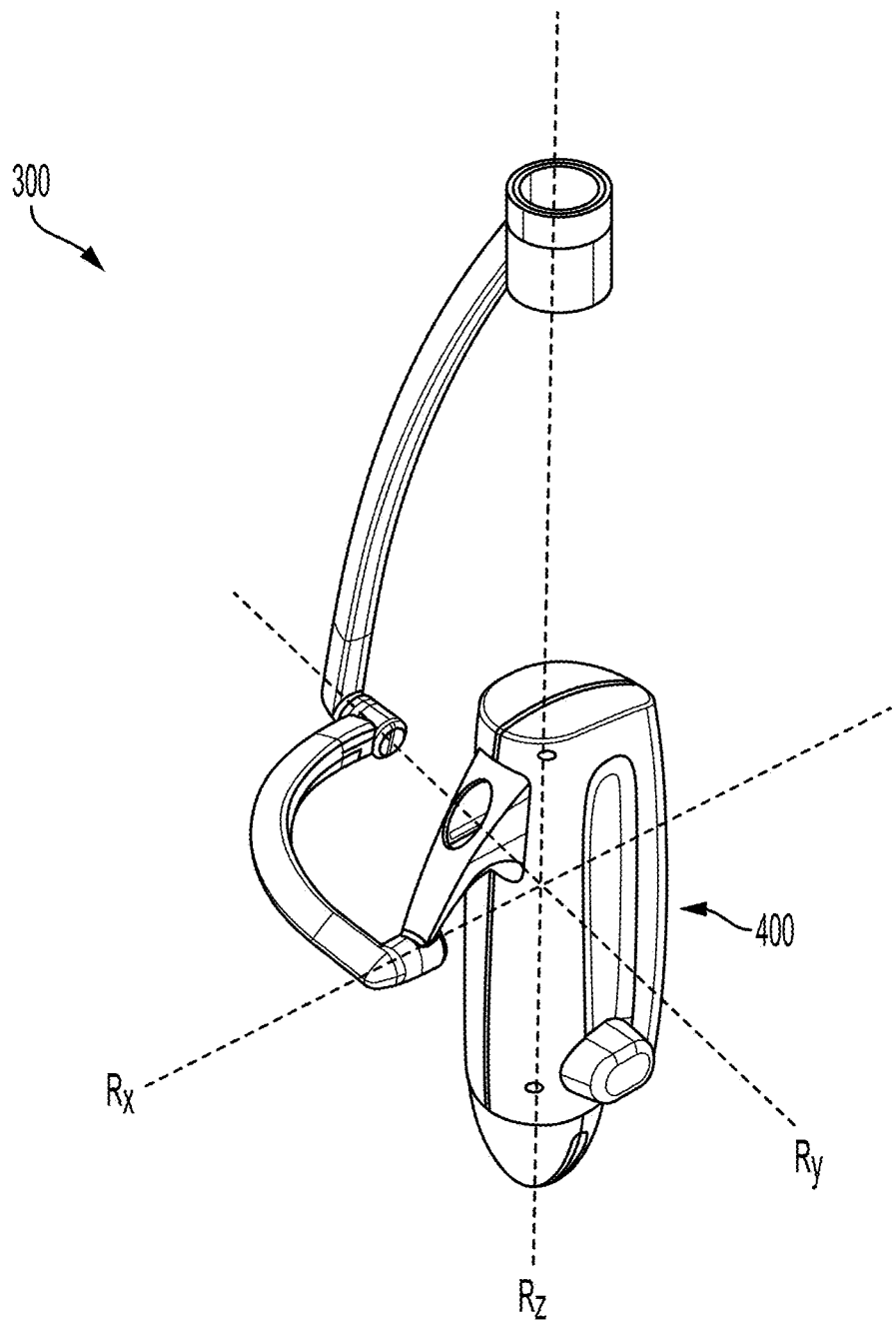
FIG. 6 is a perspective view of a connection assembly supporting a handpiece usable with the support system of FIG. 1.

The connection assembly 300 can be seen throughout the figures, for example, FIG. 6, and it operates to join the handpiece 400 to the boom assembly 200 in a way that allows for flexibility in mobility of the handpiece 400. The connection assembly 300 can have a variety of forms, and as depicted in the figures, the connection assembly 300 can take the form of a gimbal assembly that allows the rotation of the handpiece 400 in at least one, at least two, or even three degrees of freedom, all while the handpiece 400 remains coupled to the boom assembly 200. The connection assembly 300 can be designed to accommodate the size and weight of the handpiece 400 to ensure that the handpiece 400 is maneuverable with minimal effort. For example, as seen in FIG. 6, the connection assembly 300 includes three axes of rotation $R_x$, $R_y$, $R_z$ about which the handpiece 400 can rotate in respective degrees of freedom. Each of the axes of rotation $R_x$, $R_y$, $R_z$ can pass through a center of mass of the handpiece 400 to make rotation of the handpiece 400 about the axes of rotation $R_x$, $R_y$, $R_z$ as smooth as possible, and each of the axes of rotation $R_x$, $R_y$, $R_z$ can be substantially orthogonal to each other.

Figure 7:
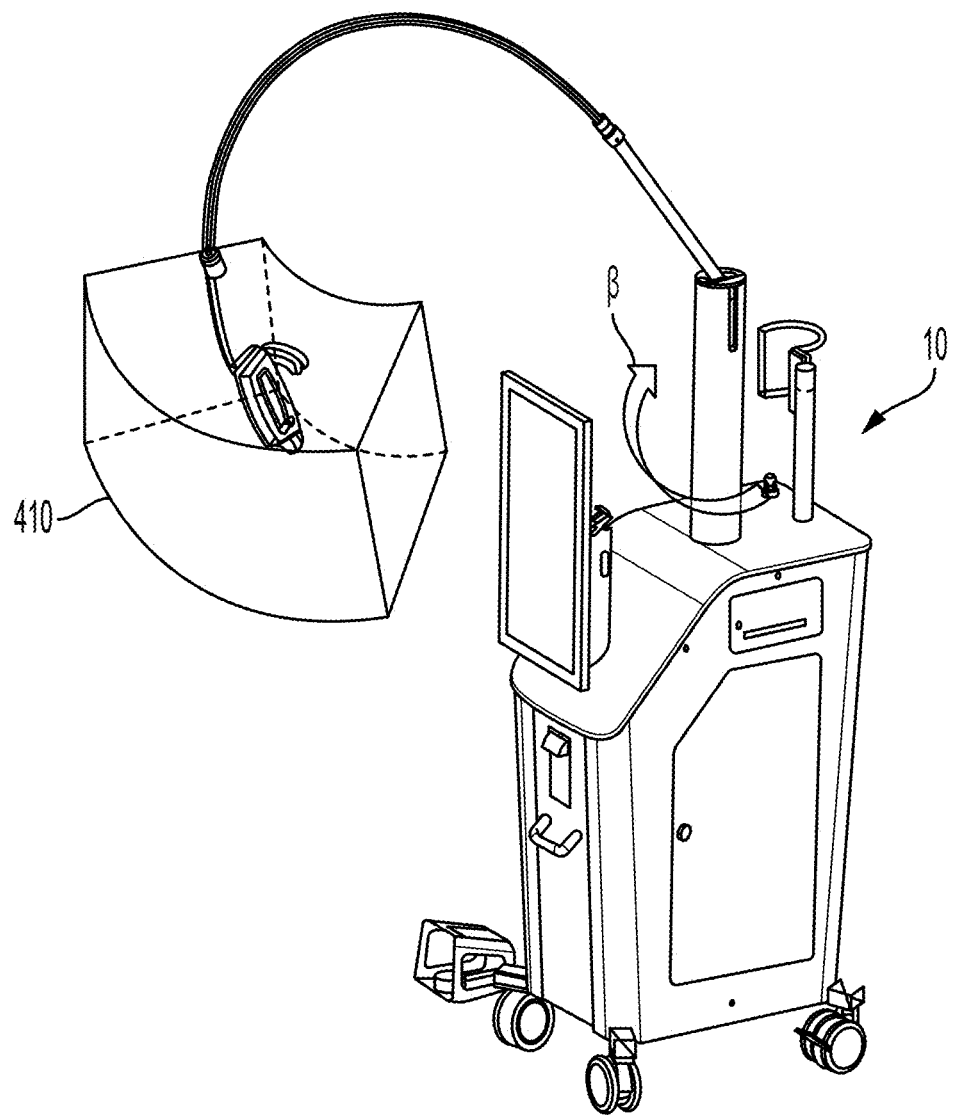
FIG. 7 is a perspective view of the support system of FIG. 1 having an envelope of minimal effort defined.
Figure 8:
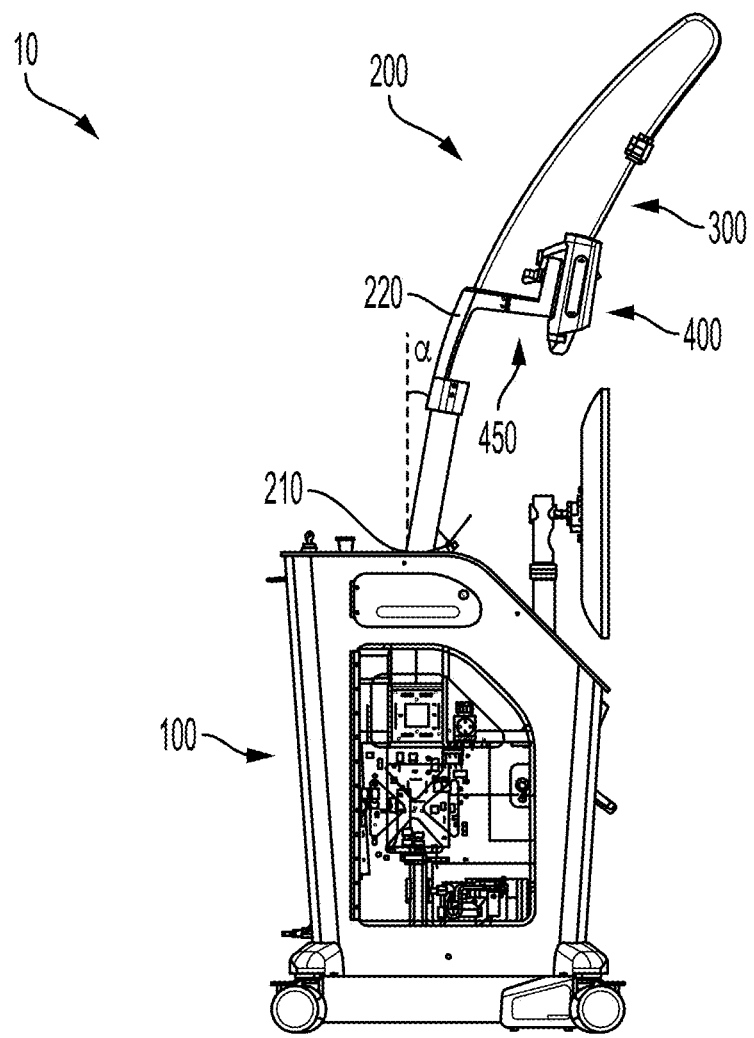
FIG. 8 is a side view of the support system of FIG. 1 in a docked position.
Figure 9:
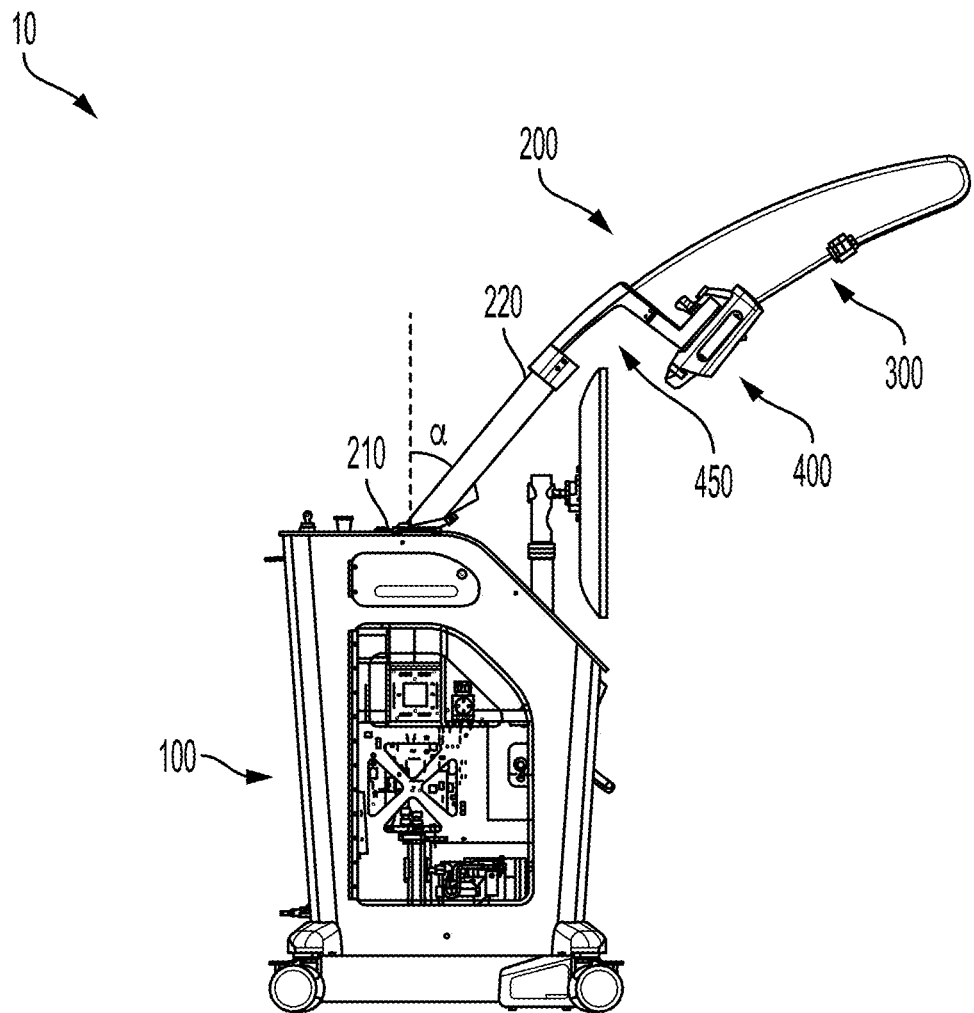
FIG. 9 is a side view of the support system of FIG. 1 in a deployed docked position.
Figure 10:
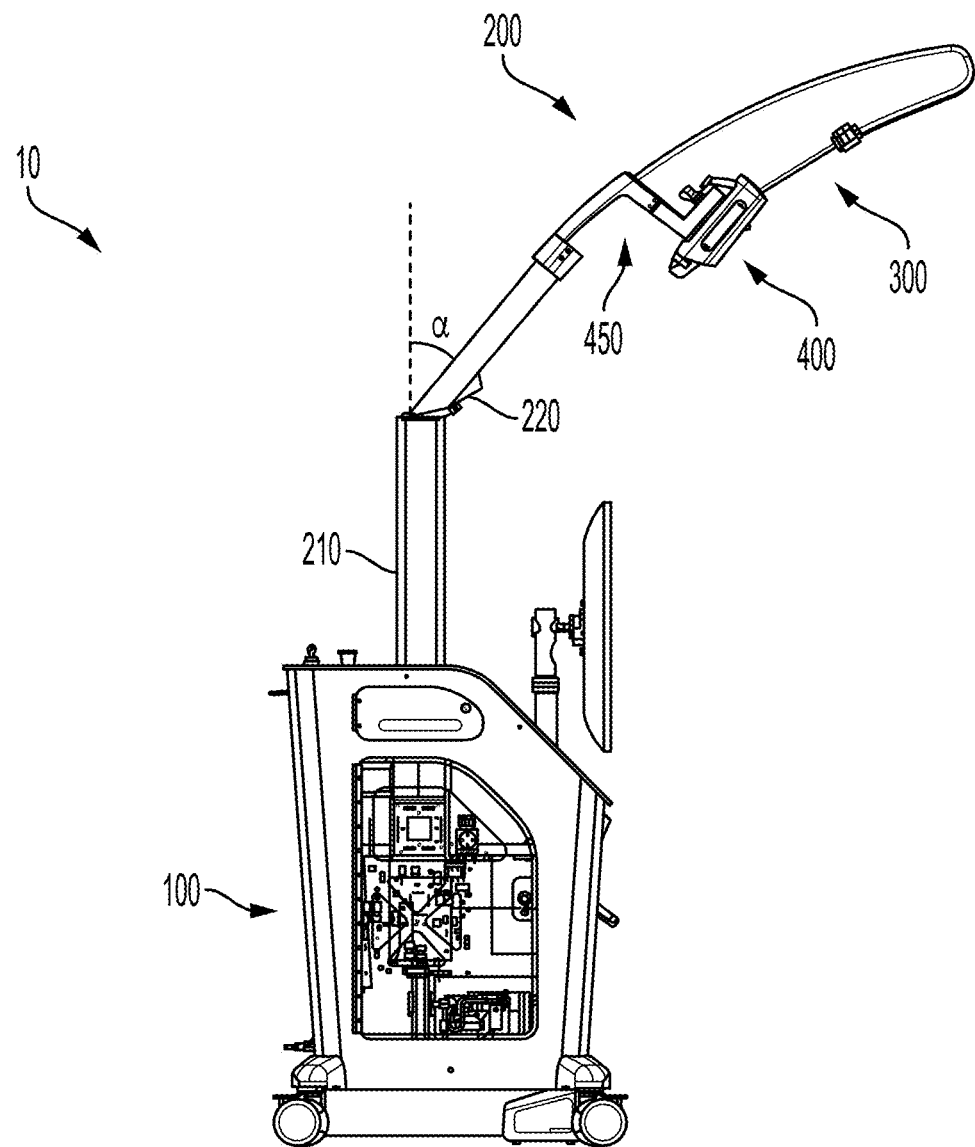
FIG. 10 is a side view of the support system of FIG. 1 in a deployed and extended docked position.

Altogether, the support system 10 can be designed to accommodate a specific handpiece 400 in order to minimize the effort required to maneuver the handpiece 400. Ultimately, the handpiece 400 will be supported in a neutral position, and a treatment operator will be able to freely move the handpiece 400 within an envelope 410 around the neutral position with minimal effort, as well as to freely move the neutral position and the envelope 410 as needed. The envelope 410 can be seen in FIG. 7. Within the envelope 410, the handpiece 400 can be maneuvered with 0.5 lbF of force or less, despite otherwise weighing between about 1.75 lbs and 2.25 lbs.

As described herein, the ways in which the support system 10 can be adjusted include: movement of the anchor base 100 on the wheels 106; extension and retraction of the lift system 210; rotation of the lift system 210; extension, retraction, and pivoting of the rigid support base 210; flexion of the flexible rod 230; and rotation of the handpiece 400 relative to the connection assembly 300. To divide these adjustments: 1) movement of the anchor base 100 on the wheels 106, and extension and retraction of the lift system 210 are adjustments that contribute to movement of the envelope 410; 2) rotation of the lift system 210 and flexion of the flexible rod 230 are adjustments that contribute to movement of the handpiece 400 within the envelope 410; and 3) rotation of the handpiece relative to the connection assembly 300 is an adjustment that contributes to orientation of the handpiece 400 in the envelope 410.

For the adjustments in group 1, the anchor base 100 can be moved on the wheels 106 as needed, and the lift system 210 can be extended and retracted about approximately a 20-inch range. For the adjustments in group 2, the lift system 210 can be rotated in a yaw direction over about a 60 degree range (±30 degrees relative to a centered position, depicted by the arrow R in FIG. 7) while a distance between the lift system 210 and the handpiece 400 is about 46 inches, and the flexible rod 230 can be moved up or down by about 3 inches, moved toward the anchor base by about 7 inches, and moved away from the anchor base 100 by about 5 inches. These movements represent exemplary ranges that define the envelope 410 for a given set up, but specific values can potentially vary beyond these numbers. Moreover, when the lift system 210 is positioned at the either limit of its angular position (i.e., ±30 degrees relative to centered position), the flexible rod 230 can be moved so that the handpiece extends about 24 inches beyond the maximum angular position, while the force required to move the handpiece remains at or below about 0.5 lbF.

In other variations, the lift system 210 can rotate further than merely a 60 degree range, and β can be a full 360 degree range at about ±180 degrees from center.

As introduced above, the support system 10 can be placed in a docked position such that the handpiece 400 is secured close to the boom assembly. As pictured in FIGS. 8-10, the handpiece is placed within a dock 450 when the support system 10 is in the docked position. As shown, the support system 10 can transition between a docked position (FIG. 8), a deployed docked position (FIG. 9), and a deployed and extended docked position (FIG. 10), all while the handpiece 400 remains secure in the dock 450. In the docked position of FIG. 8, the lift system 210 is fully retracted within the anchor base 100 so that the height of the support system 10 is minimized. The rigid support base 220 is also positioned to be as vertical as possible such that the angle α is minimized (e.g., equal to 0 degrees from vertical, 5 degrees from vertical, etc., depending upon its range). In the deployed docked position of FIG. 9, the lift system 210 is fully retracted within the anchor base 100 so that the height of the support system 10 is again minimized. The rigid support base 220 is positioned to be as horizontal as possible such that the angle α is maximized (e.g., equal to 50 degrees from vertical, 90 degrees from vertical, etc., depending upon its range). In the deployed and extended docked position, the lift system 210 is fully extended out of the anchor base 100 such that the distance D is maximized (e.g., equal to 18+ inches, 20+ inches, 30+ inches, etc., depending upon its range). The rigid support base 220 is again positioned to be as horizontal as possible. While these three docked variations are depicted, any combination of positions over any of the various ranges described herein are also possible.

The subject matter described herein can be implemented in digital electronic circuitry, or in computer software, firmware, or hardware, including the structural means disclosed in this specification and structural equivalents thereof, or in combinations of them. The subject matter described herein can be implemented as one or more computer program products, such as one or more computer programs tangibly embodied in an information carrier (e.g., in a machine readable storage device), or embodied in a propagated signal, for execution by, or to control the operation of, data processing apparatus (e.g., a programmable processor, a computer, or multiple computers). A computer program (also known as a program, software, software application, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file. A program can be stored in a portion of a file that holds other programs or data, in a single file dedicated to the program in question, or in multiple coordinated files (e.g., files that store one or more modules, sub programs, or portions of code). A computer program can be deployed to be executed on one computer or on multiple computers at one site or distributed across multiple sites and interconnected by a communication network.

The processes and logic flows described in this specification, including the method steps of the subject matter described herein, can be performed by one or more programmable processors executing one or more computer programs to perform functions of the subject matter described herein by operating on input data and generating output. The processes and logic flows can also be performed by, and apparatus of the subject matter described herein can be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processor of any kind of digital computer. Generally, a processor will receive instructions and data from a read only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. Information carriers suitable for embodying computer program instructions and data include all forms of non-volatile memory, including by way of example semiconductor memory devices, (e.g., EPROM, EEPROM, and flash memory devices); magnetic disks, (e.g., internal hard disks or removable disks); magneto optical disks; and optical disks (e.g., CD and DVD disks). The processor and the memory can be supplemented by, or incorporated in, special purpose logic circuitry.

To provide for interaction with a user, the subject matter described herein can be implemented on a computer having a display device, e.g., a CRT (cathode ray tube) or LCD (liquid crystal display) monitor, for displaying information to the user and a keyboard and a pointing device, (e.g., a mouse or a trackball), by which the user can provide input to the computer. Other kinds of devices can be used to provide for interaction with a user as well. For example, feedback provided to the user can be any form of sensory feedback, (e.g., visual feedback, auditory feedback, or tactile feedback), and input from the user can be received in any form, including acoustic, speech, or tactile input.

The techniques described herein can be implemented using one or more modules. As used herein, the term "module" refers to computing software, firmware, hardware, and/or various combinations thereof. At a minimum, however, modules are not to be interpreted as software that is not implemented on hardware, firmware, or recorded on a non-transitory processor readable recordable storage medium (i.e., modules are not software per se). Indeed "module" is to be interpreted to always include at least some physical, non-transitory hardware such as a part of a processor or computer. Two different modules can share the same physical hardware (e.g., two different modules can use the same processor and network interface). The modules described herein can be combined, integrated, separated, and/or duplicated to support various applications. Also, a function described herein as being performed at a particular module can be performed at one or more other modules and/or by one or more other devices instead of or in addition to the function performed at the particular module. Further, the modules can be implemented across multiple devices and/or other components local or remote to one another. Additionally, the modules can be moved from one device and added to another device, and/or can be included in both devices.

The subject matter described herein can be implemented in a computing system that includes a back end component (e.g., a data server), a middleware component (e.g., an application server), or a front end component (e.g., a client computer having a graphical user interface or a web browser through which a user can interact with an implementation of the subject matter described herein), or any combination of such back end, middleware, and front end components. The components of the system can be interconnected by any form or medium of digital data communication, e.g., a communication network. Examples of communication networks include a local area network ("LAN") and a wide area network ("WAN"), e.g., the Internet.

Approximating language, as used herein throughout the specification and claims, may be applied to modify any quantitative representation that could permissibly vary without resulting in a change in the basic function to which it is related. "Approximately," "substantially," or "about" can include numbers that fall within a range of 1%, or in some embodiments within a range of 5% of a number, or in some embodiments within a range of 10% of a number in either direction (greater than or less than the number) unless otherwise stated or otherwise evident from the context (except where such number would impermissibly exceed 100% of a possible value). Accordingly, a value modified by a term or terms, such as "about," "approximately," or "substantially," are not to be limited to the precise value specified. In at least some instances, the approximating language may correspond to the precision of an instrument for measuring the value. Here and throughout the specification and claims, range limitations may be combined and/or interchanged, such ranges are identified and include all the sub-ranges contained therein unless context or language indicates otherwise.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure also includes embodiments in which more than one, or all of the group members are present in, employed in, or otherwise relevant to a given product or process. Furthermore, it is to be understood that the disclosed embodiments provide all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. It is contemplated that all embodiments described herein are applicable to all different aspects of the disclosed embodiments where appropriate. It is also contemplated that any of the embodiments or aspects can be freely combined with one or more other such embodiments or aspects whenever appropriate. Where elements are presented as lists, e.g., in Markush group or similar format, it is to be understood that each subgroup of the elements is also disclosed, and any element(s) can be removed from the group. It should be understood that, in general, where the disclosed embodiments, or aspects of the disclosed embodiments, is/are referred to as comprising particular elements, features, etc., certain embodiments of the disclosure or aspects of the disclosure consist, or consist essentially of, such elements, features, etc. For purposes of simplicity those embodiments have not in every case been specifically set forth in so many words herein. It should also be understood that any embodiment or aspect of the disclosure can be explicitly excluded from the claims, regardless of whether the specific exclusion is recited in the specification. For example, any one or more active agents, additives, ingredients, optional agents, types of organism, disorders, subjects, or combinations thereof, can be excluded.

Where ranges are given herein, embodiments of the disclosure include embodiments in which the endpoints are included, embodiments in which both endpoints are excluded, and embodiments in which one endpoint is included and the other is excluded. It should be assumed that both endpoints are included unless indicated otherwise. Furthermore, it is to be understood that unless otherwise indicated or otherwise evident from the context and understanding of one of ordinary skill in the art, values that are expressed as ranges can assume any specific value or subrange within the stated ranges in different embodiments of the disclosure, to the tenth of the unit of the lower limit of the range, unless the context clearly dictates otherwise. It is also understood that where a series of numerical values is stated herein, the disclosure includes embodiments that relate analogously to any intervening value or range defined by any two values in the series, and that the lowest value may be taken as a minimum and the greatest value may be taken as a maximum. Numerical values, as used herein, include values expressed as percentages.

Although a few variations have been described in detail above, other modifications or additions are possible.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." In addition, use of the term "based on," above and in the claims is intended to mean, "based at least in part on," such that an unrecited feature or element is also permissible.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and sub-combinations of the disclosed features and/or combinations and sub-combinations of several further features disclosed above. In addition, the logic flows depicted in the accompanying figures and/or described herein do not necessarily require the particular order shown, or sequential order, to achieve desirable results. Other implementations may be within the scope of the following claims.

What is claimed is:

1. A support system for a handpiece, comprising:
a boom assembly having a rigid anchor base and a flexible rod having proximal and distal ends, the flexible rod being pivotally secured at the proximal end thereof to the rigid anchor base, the flexible rod having a flexibility that increases from the proximal end to a distal end thereof; and
a connection assembly having a proximal end configured to couple to the distal end of the flexible rod and a distal end configured to couple to the handpiece, the connection assembly being configured to enable the handpiece to rotate in at least two degrees of freedom,
wherein the boom assembly is configured to support the connection assembly and the handpiece such that the connection assembly and the handpiece rest in a neutral position.

2. The support system of claim 1 further comprising a handpiece coupled to the connection assembly.

3. The support system of claim 2, wherein the handpiece comprises a laser treatment device for medical and/or cosmetic procedures.

4. The support system of claim 1, wherein the connection assembly and handpiece are maneuverable with a minimal effort that is less than or equal to 0.5 lbF in an envelope surrounding the neutral position.

5. The support system of claim 1, wherein the connection assembly is configured to enable the handpiece to rotate in three degrees of freedom, each of the degrees of freedom being orthogonal to the other degrees of freedom.

6. The support system of claim 1, wherein the flexible rod has a consistent taper from the proximal end thereof to the distal end thereof, and wherein a flexibility of the rod increases proportionally with the constant taper from the proximal end to the distal end.

7. The support system of claim 1, wherein the flexible rod is hollow.

8. The support system of claim 1, further comprising an actuatable lift coupled to the anchor base, the actuatable lift being configured to extend in an upward direction and retract in a downward direction.

9. The support system of claim 8, wherein the actuatable lift is extendable by in the range of 18 and 30 inches.

10. The support system of claim 8, wherein the actuatable lift includes a fulcrum extension configured to support the rigid anchor base at an angle relative thereto.

11. The support system of claim 10 wherein the rigid anchor base is configured to slide relative to the fulcrum extension when the actuatable lift is extended and retracted such that the angle is configured to move in the range of 120 degrees and 180 degrees.

12. A support system for a handpiece, comprising:
a cart including an extendable lift movable between an extended position and a retracted position;
a boom assembly coupled to the extendable lift, the boom assembly including a rigid anchor base, a flexible rod coupled to a proximal end of the rigid anchor base at a proximal end thereof; and
a connection assembly coupled to a distal end of the flexible rod, the connection assembly configured to couple to the handpiece such that the handpiece can rotate in at least two degrees of freedom relative thereto.

13. The support system of claim 12, wherein the boom assembly and the connection assembly are configured to support the handpiece at a neutral position, and wherein the handpiece is maneuverable with a minimal effort that is less than or equal to 0.5 lbF in an envelope surrounding the neutral position.

14. The support system of claim 12, wherein the connection assembly is configured to enable the handpiece to rotate in three degrees of freedom, each of the degrees of freedom being orthogonal to the other degrees of freedom.

15. The support system of 12 further comprising a plurality of transport lines running along the boom assembly, wherein respective first ends of the plurality of transport lines are disposed in the cart and respective second ends are configured to connect to the handpiece.

16. The support system of claim 15, wherein the plurality of transport lines comprise at least one fluid line.

17. The support system of claim 16, wherein the at least one fluid line comprises a first fluid line configured to transport a first fluid and a second fluid line configured to transport a second fluid different than the first fluid.

18. The support system of claim 17, wherein the first fluid is a de-humidified gas and the second fluid is a coolant.

* * * * *